United States Patent [19]

Stenehjem et al.

[11] 4,280,695
[45] Jul. 28, 1981

[54] PRODUCT FOR SIMULATING A HUMAN BODY PART

[76] Inventors: Jerome C. Stenehjem, 193 E. Girard Ave., Salt Lake City, Utah 84103; Stephen C. Jacobsen, 1804 Michigan, Salt Lake City, Utah 84108

[21] Appl. No.: 120,531

[22] Filed: Feb. 11, 1980

[51] Int. Cl.³ .......................... A63J 3/00; A63J 5/00; A63H 33/00
[52] U.S. Cl. .......................................... 272/8 N; 3/1; 3/12; 46/1 R; 272/27 N
[58] Field of Search ....................... 3/1, 12, 12.6, 12.7; 272/8 N, 8 R, 1 R, 27 R, 27 N; 46/1 F, 1 R

[56] References Cited

U.S. PATENT DOCUMENTS

| | | | |
|---|---|---|---|
| 2,134,974 | 11/1938 | Hurwitz | 3/12 |
| 2,908,499 | 10/1959 | Drane | 272/8 N |
| 3,347,545 | 10/1967 | Nichols | 272/8 N |

Primary Examiner—Ronald L. Frinks

[57] ABSTRACT

A novelty or medical product simulating a human body part such as a finger, ear, nose, or the like. The body part is composed of algin, fillers, sequestriants, a calcium source and water. The body part is formed into a resilient, moist mass, and is disposed in a substantially moisture resistant pouch which has a sealable opening.

12 Claims, 1 Drawing Figure

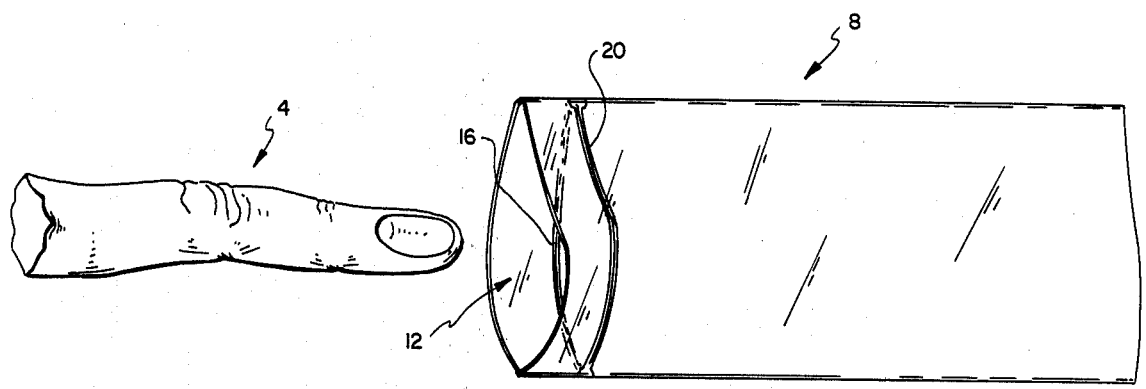

PRODUCT FOR SIMULATING A HUMAN BODY PART

BACKGROUND OF THE INVENTION

This invention relates to a novelty or medical item of a simulated human body part.

Simulated human body parts as novelty items are known, but typically the simulated part is made of rubber or plastic and does not have either the feel or realistic appearance of a human part. As a result, the usefulness of such items for novelty or for medical applications is limited. It is felt that a more realistic simulation of a human body part would require a product having a resilient and yet cold, moist feel.

SUMMARY OF THE INVENTION

It is an object of the invention to provide a new and different novelty or medical item of a simulated human body part.

It is another object of the invention to provide such an item which has a resilient moist feel when touched.

It is an additional object to provide such an item which simulates the feel and appearance of a human body part.

It is a further object of the invention, in accordance with one aspect thereof, to provide such an item which shrivels when exposed to air for a certain period of time.

It is still another object of the invention to provide such an item which may be maintained in a substantially moist, resilient state if desired.

The above and other objects of the invention are realized in a specific illustrative embodiment of a simulated body part disposed in a pouch made of substantially moisture resistant material for insertion into or removal from the pouch of the body part. The simulated body part is composed of algin, fillers, sequestriants, a calcium source, water, and preservatives, and is molded to have the appearance of a finger, ear, nose or other human part. This composition gives the body part a moist, realistic feel, and this feel is maintained when the part is kept in the pouch. The body part may also be molded or constructed in layers (laminations) or with under structures such as bones, wires, etc., located within the part.

BRIEF DESCRIPTION OF THE DRAWINGS

The above and other objects, features and advantages of the invention will become apparent from a consideration of the following detailed description presented in connection with the accompanying drawing which shows a simulated human finger and a pouch for containing the finger, all made in accordance with the principles of the present invention.

DETAILED DESCRIPTION

Referring to the drawing, there is shown a simulated human finger 4 made of a composition to be described hereinafter, and a bag or pouch 8 having an interior cavity into which the finger 4 would be inserted. The pouch 8 includes an opening 12 at one end thereof to allow insertion into and removal from the pouch of the finger 4. The pouch 8 is constructed of a moisture resistance material such as polyethylene, and, advantageously, the material is clear to allow viewing the finger 4 when in place inside the pouch. The pouch 8 further includes closure elements comprised of a pair of mateable strips 16 and 20 formed in the pouch material so that when the opening 12 is closed the elements 16 and 20 mate and sealingly join. An example of such closure is the so-called zip-lock arrangement which allows for joining two mating elements by simply pressing the elements together and for unjoining the elements by pulling them apart. It should be understood that a variety of other closure arrangements could also be provided in the pouch 8 for the purpose of allowing the opening and closing of the pouch. Ideally, the closure arrangement substantially prevents moisture from escaping from the pouch 8 when in a closed configuration.

Of course, the finger 4 (or other body part) could be placed in a pouch or bag which is thereafter permanently sealed, such as by heat sealing. Then, when removeal is desired, the bag would simply be torn or broken to allow removal.

The finger 4 is molded of a material composed of algin, fillers, sequestriants, preservatives, calcium source and water. The composition of algin, fillers, sequestriants and calcium source may be purchased commercially under the name "alginate" from sources such as Bosworth Company and Coe Laboratories. The filler in the composition above may be diatomacious earth, magnesium carbonate, or similar materials. The calcium source may be calcium chloride, calcium carbonate, or other similar materials. The sequestriants may be tetrasodium pyrophosphate or other similar materials which delays linking or hardening of the mixture.

The alginate and preservatives are mixed with water until the mixture is free of lumps and then poured or injected into a mold to form the desired body part. It has been found that for about 50 milliliters of water, 12 grams of alginate will yield a simulated body part which is resilient and yet fairly sturdy. After the mixture is placed in the mold, it is allowed to set for a period of time until the mixture hardens, for example, about five minutes or more. The mold could be made of a variety of materials including RTV Silicone Rubber, using conventional techniques.

Since algin is a plant product (made from a type of seaweed) there may be a problem with mold growing on the novelty product. In order to prevent this, an antibacterial, antifungus and antimold substance may be added to the composition. For example sodium benzoate, potassium sorbate, or other conventional food preservative may be added.

In order to obtain a flesh-like color for the simulated human body part, a pink coloring agent, such as iron oxide coloring, may be added to the composition. Such coloring agent advantageously is oil soluble and not water soluble so that the color will be less likely to come off on a person's hands when the product is handled. Alternatively alginate may be purchased as either pink or white and if equal portions are mixed together, the coloring is very similar to a flesh color.

Exemplary proportions for the composition of the product using the above mentioned ingredients are as follows:

| Component Part | Percent by Weight |
| --- | --- |
| Water | 79.8 |
| alginate | 20.0 |
| sodium benzoate | .1 |
| potassium sorbate | .1 |

The above composition may be varied to achieve any desired consistency and firmness of the finished product. For example, reducing the amount of alginate will result in the product being softer and less durable, whereas increasing the amount of alginate will increase the firmness of the product. If the amount of preservative is increased, then the product tends to become grainy whereas if the amount of preservative is reduced, then the chance of mold or fungus developing is increased.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modfications and arrangements.

What is claimed is:

1. A product simulating human body parts such as fingers, ears, noses and the like comprising
   a pouch made of a substantially moisture resistant material, and
   a simulated body part disposed in the pouch, said part being formed to have the appearance of a human body part, and being composed of algin, fillers, calcium source, sequestriants and water.

2. A product as in claim 1 wherein said pouch is made of a substantially clear material.

3. A product as in claim 1 wherein the proportion of water to other materials in the composition is about 50 milliliters of water to about 12 grams of other materials.

4. A product as in claim 1 wherein said simulated body part is further composed of a non-water-soluble coloring material.

5. A product as in claim 4 wherein said coloring material is comprised of an oil-soluble material.

6. A product as in claim 1 wherein said simulated body part is further composed of a food preservative.

7. A product as in claim 6 wherein the food preservative constitutes between 0.1 and 0.2 percent by weight of the composition.

8. A product as in claim 1 wherein said pouch includes an opening, and means for selectively sealing and unsealing said opening.

9. A product simulating a human body part composed of a mixture of algin, fillers, sequestrants, calcium source and water in proportions such that the mixture has the characteristic of an elastic solid, said solid being formed in the shape of a human body part.

10. A product as in claim 9 wherein the proportion of water to other materials in the mixture is about 50 milliliters of water to about 12 grams of such other materials.

11. A product as in claim 9 wherein said mixture further includes a non-water-soluble coloring material.

12. A product as in claim 9 wherein said mixture further includes a food preservative.

* * * * *